United States Patent [19]

Evans et al.

[11] 4,038,405

[45] July 26, 1977

[54] ACARICIDAL TRIFLUOROMETHYL-1,2,4-TRIAZOLES

[75] Inventors: John James Alexander Evans, East Brighton; George Holan, Brighton, both of Australia

[73] Assignee: Commonwealth Scientific and Industrial Research Organization, Campbell, Australia

[21] Appl. No.: 522,626

[22] Filed: Nov. 11, 1974

[30] Foreign Application Priority Data

Nov. 13, 1973 Australia .......................... 5638/73

[51] Int. Cl.$^2$ .................. C07D 249/08; A01N 9/22

[52] U.S. Cl. ............................ 424/269; 424/263; 260/295 AM; 260/296 R; 260/304 R; 260/308 R

[58] Field of Search ............... 260/308 R; 424/269

[56] References Cited

PUBLICATIONS

Schmelzer et al., Chem. Abstracts, vol. 66, Abstract No. 10907m (1967).

Primary Examiner—Raymond V. Rush
Attorney, Agent, or Firm—Bacon & Thomas

[57] ABSTRACT

3-Trihalomethyl-1,2,4-triazoles either unsubstituted or having substituents in the 4 and/or 5, 1 and/or 5, and 2 and/or 5 positions; and methods for their preparation. Some of the compounds show biological activity; others have acaricidal activity.

4 Claims, No Drawings

ACARICIDAL TRIFLUOROMETHYL-1,2,4-TRIAZOLES

The invention is concerned with new substituted 3-trihalomethyl-1,2,4-triazoles possessing biological activity. The invention also includes methods for the preparation of the new compounds.

The triazole nucleus can have three tautomeric structures, allowing for up to two substituents to be introduced in addition to the trihalomethyl group. The compounds (I) provided by the present invention are thus represented by the three general structures

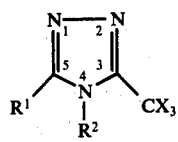
(Ia)

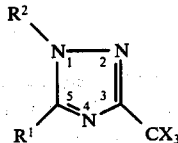
(Ib)

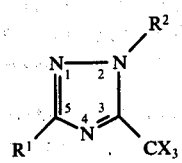
(Ic)

in which
$X_3$ represents $F_3$ or $F_2Cl$;
$R^1$ is H, alkyl or cycloalkyl up to $C_{12}$ which may be further substituted with chlorine or bromine groups, aryl or heteroaryl which may be further substituted with (lower) alkoxy, (lower) alkyl, halogen or nitro groups;
$R^2$ is H, alkyl or cycloalkyl up to $C_{12}$, aryl or heteroaryl which may be further substituted with (lower) alkoxy, (lower) alkyl, halogen or nitro.

The preferred aryl group is the phenyl group. Preferred heteroaryl groups include pyridyl, benzimidazolyl and benzothiazolyl.

Although 1,2,4-triazoles are well known as a class, none substituted in the 3 position with a trifluoro- or chlorodifluoro-methyl group have been described previously, nor has biological activity been attributed to any such compounds.

The compounds of the invention may be prepared by the following methods, which also form a part of the invention.

A. Triazoles substituted in the 4 and/or 5 positions (formula Ia) may be produced by the reaction of a trihaloacethydrazide (II) with an appropriately substituted imino acid derivative (III), as shown by the general equation

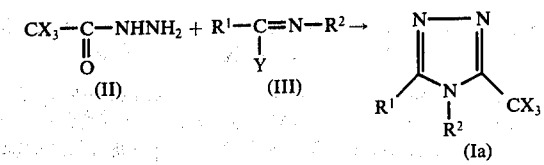

where $R^1$, $R^2$ and $X_3$ are as described above, Y is OR or Cl or $NH_2$, where R is lower alkyl.

Usually it is convenient to prepare the hydrazide (II) in situ from the trihaloacetate and hydrazine hydrate and then add the imidate ester or imidoyl chloride (III). In the initial stage of the reaction, the temperature should preferably be kept low to prevent decomposition, at least below about 10° C. In order to complete the reaction, higher temperature is needed. This may be done conveniently by evaporating off the initial solvent, which is conveniently methanol, ethanol, or other ow boiling oxygen-containing solvent, and heating the residue. The heating step is either carried out at elevated temperature in a high boiling solvent such as xylene, with continuous removal of water, or alternatively at lower temperature in acid conditions. Glacial acetic acid is a convenient acid for the purpose. In the case of reaction with an imidoyl chloride, the splitting out of hydrochloric acid provides an acid medium and the original reaction mixture may be refluxed to complete the reaction.

B. In order to produce triazoles having substituents in the 1 and/or 5 positions (formula Ib), it is convenient to react a substituted hydrazine (IV) with a trihaloacetamidine hydrohalide, acetate or other soluble salt (V) in order to form an amidrazone (VI), and then react this with an orthoester (VII), according to the following general equations:

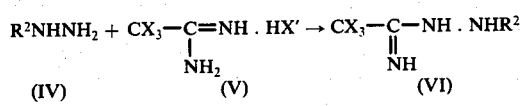

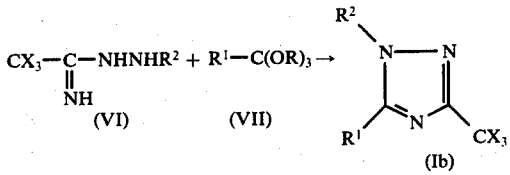

where $R^1$, $R^2$, $X_3$ and R are as described above, and $HX'$ is the acid residue of the salt (V).

The first step usually proceeds readily by mixing the reactants in a solvent such as methanol or ethanol, preferably at low temperature to avoid decomposition. Removal of the solvent leaves the amidrazone (VI) plus ammonium chloride, the latter being removed with water. The reaction with the ortho ester is most simply carried out by refluxing the amidrazone in excess of the ester until reaction is finished, and then distilling off the excess ester.

C. In order to obtain the trihalotriazole substituted in the 2 or the 2 and 5 positions (formula Ic), it is usually necessary to prepare 3-trihalomethyl-1,2,4-triazole or the appropriate 5-substituted 3-trihalomethyl-1,2,4-triazole and then introduce the 2-substituent by a direct method, such as alkylation with an akyl iodide. This will generally produce a mixture of isomers, from which the 2-substituent can be separated by appropriate methods such as liquid chromatography.

The parent compounds, 3-chlorodifluoromethyl-1,2,4-triazole and 3-trifluoromethyl-1,2,4-triazole are conveniently prepared by decarboxylation of the hydrolyzed 5-trichloromethyl derivative, by heating with a suitable base in one step. The trichloromethyl compound may be prepared by the general method (A) described above. (D) A further general method for the production of 5(3)-substituted 3(5)-trifluoromethyl-1,2,4-triazoles (formula Ia; $R^2=H$) involves the reaction of the appropriately substituted acid hydrazide (IX) with a trifluoroacetamidine salt (usually the hydrochloride (X)) in a suitable solvent (usually ethanol). The intermediate product (XI) is refluxed in aqueous alkali to give the final product (Ia).

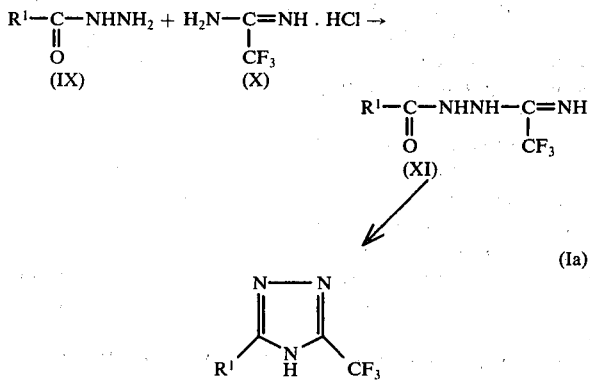

E. In addition to the above, methods involving the direct substitution of groups into the triazole nucleus may provide the most convenient method of preparation for some of the compounds I. For example, a m-nitro phenyl derivative is best prepared by making the phenyl derivative by one of the methods (A) (B) (C) or (D) described above and then nitrating the resulting triazole compound when the m-nitro derivative is preferentially formed. Halogenation and other reactions can be carried out similarly.

Compounds in which $X_3$ represents $Cl_3$ are, as indicated above, useful as intermediates in the preparation of the other compounds.

The compounds in which $X_3$ represents $F_3$ or $F_2Cl$ are inhibitors of biological oxidation. More specifically they show activity as uncouplers of oxidative phosphorylation; they inhibit energy transfer in mitochondria, they inhibit monoamine oxidase and also inhibit the growth of yeasts. These compounds therefore are of potential value in pest control and they have been found to have acaricidal activity.

In this specification, where the context permits, the word "acaridical" is used to imply activity against arthropods, such as spiders, centipedes and the like, and especially to the order *Acaridae* which includes the mites and ticks. The word "acaricide" is similarly used.

The acaricidally active compounds of this invention have been found to be active against larvae of the Queensland cattle tick (*Boophilus microplus*), which is a serious pest in Australia, the the two-spotted spider mite (*Tetranychus urticae*).

The compounds of the invention may be incorporated in a suitable insert solvent, or mixture of solvents, or in a solid mixture with other substances, such as wetting, dispersing and sticking agents. The compounds may be employed in such compositions either as the sole toxic agent or in combination with other acaricides or with insecticidal fungicidal or bactericidal agents, to provide compositions useful for agricultural and veterinary dusts, sprays, and dips, or for horticultural or household use. The compounds maybe dissolved or suspended in suitable organic or aqueous media to provide solutions or dispersions of enhanced utility. The compounds may also be mixed with an inert, finely divided, solid diluent or carried such as bentonite, bole, talc, charcoal, pumice, calcium carbonate and the like. The compounds maybe admixed in its original form or in solution.

It is to be understood that the invention includes all of the above mentioned compositions and other variations thereof as would be evident to persons skilled in the art.

The invention also includes a method for the control of arthropods, especially Acaridae, which comprises contacting the arthropods with, or applying to their locus, a compound or composition in accordance with the invention.

In the preparative methods described, the initial reaction usually results in the formation of an amidrazone.

Using preparative method (A), the amidrazone (VIII) is formed as follows:

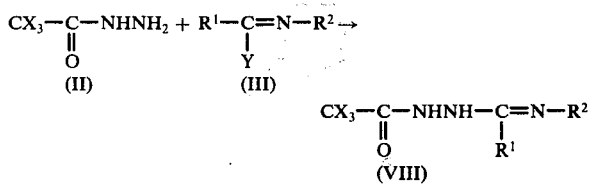

In methods (B) and (D), the formation is as shown earlier. The amidrazones of formulae (VI), (VIII) and (X) as stated and defined above are novel and they and their methods of preparation constitute further aspects of this invention. The compounds (VI) (VIII) and (X) are valuable intermediates for preparation of the compounds (I).

The following examples illustrate the methods of preparation and activities of compounds of the invention.

EXAMPLE 1

Preparation of 4-Phenyl-3-trifluoromethyl-1,2,4-triazole (Method A - Thermal reaction)

Ethyl trifluoroacetate (2.9 g) was added to hydrazine hydrate (1.1g, 99 - 100%) in methanol (20 ml) at 5°-10° and stirred for 15 min. Methyl-N-phenyl formimidate (2.7 g) was added keeping the temperature below 10° for 1 hr. and then at room temperature for another hr. The mixture was evaporated to dryness under reduced pressure and the residue refluxed in xylene (100 ml) for 4 hr. with continuous removal of water.

Evaporation under reduced pressure and crystallization of the oily residue from methanol/water gave 4-phenyl-3-trifluoromethyl-1,2,4-triazole (2.2 g, 53%) m.p. 80° (Found: C, 50.62%; H,2.86%; F, 26.5%; N, 19.82%. $C_9H_6F_3N_3$ requires: C,50.71%; H, 2.84%; F, 26.7%; N, 19.71%.) $\delta(CDCl_3)$: 8.52 (1H,s); 7.67 (5H, m), m/e, 213.)

The precipitate formed initially analyzed for 4-phenyl-1-trifluoroacetyl formamidrazone hydrate m.p. 177° (from benzene). (Found: C, 43.77%; H, 3.67%; F, 22.7%; N, 17.35%. $C_9H_{10}F_3N_3O_2$ requires: C, 43.38%, H, 4.05%; F, 22.9%.)

EXAMPLE 2

Preparation of 4-phenyl-3-trifluoromethyl-1,2,4-triazole (Method A - acid catalyzed reaction)

Ethyl trifluoroacetate (14.4 g) was added to hydrazine hydrate (5.1 g, 99-100%) in methanol (100 ml) at 5°-10° and stirred for 30 min. Ethyl-N-phenyl formimidate (14.9 g) was added keeping the temperature below 10° for 1 hr. and then at room temperature for another hour; a precipitate formed after approximately 10 min. The mixture was evaporated to dryness under reduced pressure and the residue heated at 90°–100° with glacial acetic acid (100 ml) for 1 hr. Evaporation under reduced pressure and crystallization of the residue from methanol/water gave 4-phenyl-3-trifluoromethyl-1,2,4-triazole (13.6 g, 63.9%) m.p. 80°.

EXAMPLE 3

Preparation of 4-(4-chlorophenyl)-3-trifluoromethyl-1,2,4-triazole

Prepared from ethyl-N-(4-chlorophenyl)formimidate, ethyl trifluoroacetate and hydrazine hydrate using the method of Example 1, in 50% yield m.p. 108° (from ethanol/water). (Found: C, 44.03%; H, 2.11%; Cl, 14.00%; F, 23.2%; N, 16.82%. $C_9H_5ClF_3N_3$ requires C, 43.66%; H, 2.04%; Cl, 14.32%; F, 23.0%; N 16.97%) $\delta(CDCl_3)$: 8.37 (1H, s); 7.50 (4H, m). m/e, 247 and 249.

EXAMPLE 4

Preparation of 4-(2-methylphenyl)-3-trifluoromethyl-1,2,4-triazole

Prepared from ethyl-N-(2-methylphenyl) formimidate, ethyl trifluoroacetate and hydrazine hydrate using the method of Example 2, in 76.5% yield m.p. 75° (from petroleum spirit 60°–80° ). (Found: C, 53.03% H, 3.39%; F, 24.9%; N, 18.21%. $C_{10}H_8F_3N_3$ requires: C, 52.86%; H, 3.55%; F, 25.1%; N, 18.50%.) $\delta(CDCl_3)$; 8.40 (1H, s); 7.43 (4H, m); 2.10 (3H, s). m/e, 227.

EXAMPLE 5

Preparation of 4-(2-t-butylphenyl)-3-trifluoromethyl-1,2,4-triazole

Prepared from ethyl-N-(2-tbutylphenyl) formimidate, ethyl trifluoroacetate and hydrazine hydrate using the method of Example 2, in 32.2% yield m.p. 120° (from ethanol/water). Found: C, 58.09%; H, 5.25%; F, 21.3%; N, 15.43%. $C_{13}H_{14}F_3N_3$ requires: C, 57.98%; H, 5.24%; F, 21.2%; N, 15.61%.) $\delta(CDCl_3)$; 8.42 (1H, s); 7.40 (4H,m); 1.20 (9H, s). m/e, 269.

EXAMPLE 6

Preparation of 4-(2-methoxyphenyl)-3-trifluoromethyl-1,2,4-triazole

Prepared from ethyl ethyl-N-(2-methoxyphenyl) formimidate, ethyltrifluoroacetate and hydrazine hydrate using the method of Example 2, in 58.9% yield m.p. 62° (from methanol/water). (Found: C,49.48%; H, 3.29%; F, 23.4%; N, 17.53%. $C_{10}H_8F_3N_3O$ requires: C, 49.41%; H, 3.32%; F, 23.5%; N, 17.29%). $\delta(CDCl_3)$: 8.37 (1H, s); 7.40 (4H, m); 3.90 (3H, s). m/e, 243.

EXAMPLE 7

Preparation of 4-(4-ethoxyphenyl)-3-trifluoromethyl-1,2,4-triazole

Prepared from ethyl N-(4-ethoxyphenyl) formimidate, ethyltrifluoroacetate and hydrazine hydrate using the method of Example 2, in 59% yield m.p. 70° (from pet. spirit 60°–80° ). (Found: C, 51.68%; H, 3.92%; F, 21.5%; N, 16.38%. $C_{11}H_{10}F_3N_3O$ requires: C, 51.36%; H, 3.52%; F, 22.2%; N, 16.34%.) $\delta(CDCl_3)$; 8.25 (1H, s); 7.12 (4H,q); 4.08 (2H, q); 1.57 (3H, t), m/e, 257.

EXAMPLE 8

Preparation of 4-(4-t-butyl phenyl)-3-trifluoromethyl-1,2,4-triazole

Prepared from ethyl-N-(4-t-butylphenyl) formimidate, ethyl trifluoroacetate and hydrazine hydrate using the method of Example 2, in 44.6% yield m.p. 134° (from methanol/water). (Found: C, 58.35%; H, 5.49%; F, 20.9%; N, 15.95%; $C_{13}H_{14}F_3N_3$ requires: C, 57.98%; H, 5.24%; F, 21.2%; N, 15.61%.) $\delta(CDCl_3)$: 8.27 (1H, s); 7.40 (4H, q); 1.17 (9H, s). m/e, 269.

EXAMPLE 9

Preparation of 4-(2,4-Dimethylphenyl)-3-trifluoromethyl-1,2,4-triazole

Prepared from ethyl-N-(2,4-dimethylpheny) formimidate, ethyl trifluoroacetate and hydrazine hydrate using the method of Example 2, in 55.7% yield m.p. 77° (from pet. spirit 60°–80° ). (Found: C, 55.03%; H, 4.25%; F,23.3%; N, 17.62%. $C_{11}H_{10}F_3N_3$ requires: C, 54.77%; H, 4.18%; F, 23.6%; N, 17.42%.) $\delta(CDCl_3)$: 8.32 (1H, s); 7.20 (3H, m); 2.47 (3H, s); 2.07 (3H, s), m/e, 241.

EXAMPLE 10

Preparation of 4-(4-Chloro2-methylphenyl)3-trifluoromethyl-1,2,4-triazole

Prepared from ethyl-N-(4-chloro-2-methylphenyl) formimidate, ethyl trifluoro acetate and hydrazine hydrate using the method of Example 2 in 70% yield m.p. 90° (from pet, spirit 60°–80° ). (Found: C, 45.84%; H, 2.74%; Cl, 13.8%; F, 21.7%; N, 16.06%; $C_{10}H_7ClF_3N_3$ requires: C, 45.91%; H, 2.70%; Cl, 13.6%, F, 21.8%; N, 16.06%.) $\delta(CDCl_3)$; 8.30 (1H, s); 7.33 (3H, m); 2.07 (3H, s), m/e, 261 and 263.

EXAMPLE 11

Preparation of 3-Methyl-4-phenyl-5-trifluoromethyl-1,2,4-triazole

Ethyl trifluoroacetate (4.3 g) was added to hydrazine hydrate (1.5 g, 99–100%) in methanol (30 ml) at 5°–10° and stirred for 15 min. Ethyl-N-phenylacetimidate (3.9 g) was added keeping the temperature below 10° for 1 hr and then at room temperature for another hour. The mixture was evaporated to dryness under reduced pressure and the residue heated at 90°–100° with glacial acetic acid (50 ml) for 1 hr. Evaporation under reduced pressure and crystallization of the residue from methyl cyclohexane gave 3-methyl-4-phenyl-5-trifluoromethyl-1,2,4-triazole (2.8 g, 41.2%) m.p. 118°. (Found: C, 52.73%; H, 3.72%; F, 25.3%; N, 18.78%. $C_{10}H_8F_3N_4$ requires: C, 52.87%; H, 3.55%; F, 25.1%; N, 18.50%). $\delta(CDCl_3)$: 7.47 (5H, m); 2.33 (3H, s). m/e, 227.

EXAMPLE 12

Peparation of 3,4-bis(4-chlorophenyl)-5-trifluoromethyl-1,2,4-triazole

Ethyl trifluoroacetate (2.9 g) was added to hydrazine hydrate (1.1 g, 99–100%) in methanol (20 ml) at 5°–10° and stirred for 15 min. N-(4-chlorophenyl)-4-chlorobenzimidoyl chloride (5.7 g) was added keeping the temperature below 5° for 3 hr and then at reflux for 1 hr 3,4-bis(4-chlorophenyl)-5-trifluoromethyl-1,2,4-triazole crystallized on cooling (4.1 g, 57.8%) m.p. 184°. (Found: C, 50.54%; H, 2.40%; Cl, 19.6%; F, 15.8%; N, 11.54%. $C_{15}H_8Cl_2F_3N_3$ requires: C, 50.30%; H, 2.25%; Cl, 19.8%; F, 15.9%; N, 11.73%) δ(CDCl$_3$); 7.43(m).

EXAMPLE 13

Preparation of 1-phenyl-3-trifluoromethyl-1,2,4-triazole (Method B)

Trifluoroacetamidine hydrochloride (4.95 g) was added to phenylhydrazine (3.60 g) in methanol (30 ml) and stirred at 5°–10° for 30 min - ammonium chloride precipitated from solution. Concentration under reduced pressure and addition of water gave 1-phenyltrifluoroacetamidrazone (5.52 g, 81.5%) m.p. 68° (from pet. spirit 60°–80° ). (Found: C, 47.33%; H, 4.07%; F, 28.3%; N, 21.02%. $C_8H_8F_3N_3$ requires: C, 47.29%; H, 3.97%; F, 28.1%; N, 20.68%). m/e, 203.

1-Phenyltrifluoroacetamidrazone (8.80 g) was heated at reflux with triethylorthoformate (150 ml) for 36 hr. Fractionation, after removal of excess triethylorthoformate gave 1-phenyl-3-trifluoromethyl-1,2,4-triazole (7.42 g, 80.8%) b.p. 95° at 0.5 mm. (Found: C, 50.41%; H, 3.09%; F, 26.8%; N, 20.02%. $C_9H_6F_3N_3$ requires: C, 50.71%; H, 2.84%; F, 26.7%; N, 19.71%) $n_D^{20}$, 1.4986. δ(CDCl$_3$); 8.60 (1H, s); 7.58 (5H, m). m/e, 213.

EXAMPLE 14

Preparation of 4-(3-Nitrophenyl)-3-trifluoromethyl-1,2,4-triazole (Method D)

Fuming nitric acid (0.5 g) was added to 4-phenyl-3-trifluoromethyl-1,2,4-triazole (1.06 g) (see Example 1) in concentrated sulphuric acid (15 ml) at 5°–10° and then slowly heated to 85° for 1 hr. The cooled acid solution was poured onto ice to give 4-(3-nitrophenyl)-3-trifluoromethyl-1,2,4-triazole (0.82 g, 63.4%) m.p. 142° (from benzene). Found: C, 41.70%, H, 2.13%; F, 22.1%; N, 21.43%. $C_9H_5F_3N_4O_2$ requires: C, 41.87%; H, 1.95%; H, 1.95%; F,22.1%; N, 21.70%). High resolution nmr spectroscopy indicated substitution in the m-position of the phenyl ring. m/e, 259.

EXAMPLE 15

Preparation of 3(5)-trichloromethyl-5(3)-trifluoromethyl-1,2,4,-triazole (Method B)

The compound may be made by either of the following methods:

I. A solution of methyl-2,2,2-trichloroacetimidate (7.04 g) and trifluoroacethydrazide (5.12 g) in diethyl ether (50 ml) was stirred at room temperature for 2 days. Evaporation to dryness and crystallization from hot benzene gave 3(5)-trichloromethyl-5(3)-trifluoromethyl-1,2,4-triazole (8.20 g, 80.5%), m.p. 168° (rapid heating). Found: C, 18.98%; H, 0.37%; Cl, 41.49%; F, 22.95%; N, 16.36%. Calc. for $C_4HCl_3Fe_3N_3$: C, 18.73%; H, 0.39%, Cl, 41.48; F, 23.00%; N, 16.39%.

II. Ethyl trifluoroacetate (14.30 g) was added to hydrazine hydrate (5.0 g, 98–100%) in methanol (20 ml) with stirring at 0°–5°. After evaporation to dryness under reduced pressure at less than 40°, methyl-2,2,2-trichloroacetimidate (17.60 g) in benzene (200 ml) was added and the mixture refluxed for 2 hr. The residual oil, after removal of benzene, was carefully treated with concentrated sulphuric acid (100 ml, d. 1.84) and heated at 75° for 5 min. The triazole was liberated by pouring the acid solution into ice-water (13.3 g, 52.1%) m.p. 168° (from benzene).

EXAMPLE 16

Preparation of 3-trifluoromethyl-1,2,4-triazole (Method C)

3(5)-trichloromethyl-5(3)-trifluoromethyl-1,2,4-triazole (2.50 g) prepared as in Example 17 was heated on the water bath for 2 hr with aqueous potassium hydroxide (1.7 g in 30 ml of water), acidified with acetic acid and evaporated to dryness. The residue was extracted with hot chloroform (200 ml), filtered and evaporated to dryness to give 3-trifluoromethyl-1,2,4-triazole(0.92 g, 70%), m.p. 89° (from benzene). nmr (DMSO d$_6$, δ p.p.m.); 8.43 (singlet). Molecular weight (m/e) 137. Found: C, 26.04%, H, 1.53%; F, 41.5%; N, 30.50%. Calc. for $C_3H_2F_3N_3$: C, 26.29%; H, 1.47%; F, 41.6%; N, 30.66%.

EXAMPLE 17

Preparation of 2-(3-trifluoromethyl-1,2,4-triazol-5-yl)benzthiazole

A solution of o-aminothiophenol (1.25g), 3(5)-trichloromethyl-5(3)-trifluoromethyl-1,2,4-triazole (2.60g) and triethylamine (3.03g) in 1,2-dimethoxyethane (50 ml) was stirred at room temperature for 3 days. Dilution with water and filtration of the precipitate gave the benzthiazole (1.81g, 66.7%) m.p. 254° (from diethyl ether petroleum spirit; b.p. 60°–80° ). (Found: C 44.3, H, 2.1, F, 21.0; N, 20.9; F, 11.7. $C_{10}H_5F_3N_4S$ requires: C, 44.4; H, 1.9; F, 21.1; N, 20.7; S, 11.9%); m/e 270 (M+).

EXAMPLE 18

Preparation of 2-(3-trifluoromethyl-1,2,4-triazol-5-yl)benzimidazole

The benzimidazole was prepared from o-phenylenediame (0.75g), 3(5)-trichloromethyl-5(3)-trifluoromethyl-1,2,4-triazole (1180g) and triethylamine (2.20g) in 1,2-dimethoxyethane (20ml) using the method of Example 17. Yield 1.4g, 65.2%; m.p. 247° (from chloroform) (Found: C, 47.5; H, 2.4; F, 22.5; N, 27.3. $C_{10}H_6N_5F_3$ requires: C, 47.4; H, 2.4; F, 22.5; N 27.6%); m/e 253 (M+).

EXAMPLE 19

Preparation of 3(5)-chlorodifluoromethyl-1,2,4-triazole

Ethyl chlorodifluoroacetate (4.5g) was added to hydrazine hydrate (1.25g) in ethanol (35ml) and stirred at 5° to 1 hr. Formamidine acetate (2.61g) in ethanol (10ml) was added and stirred for 1.5 hr. After evaporation to dryness at reduced pressure the residue was heated in glacial acetic acid (50 ml) at 100° for 5 hr. Evaporation to dryness and extraction with chloroform gave the triazole δ(CDCl$_3$) 8.42 (1H, S, H—C); m/e 153,155 (M+), 118 (M+-HCl).

EXAMPLE 20

Preparation of (a) 3(5)-(1-adamantyl)-5(3)-trifluoromethyl-1,2,4-triazole

Trifluoroacetamide hydrochloride (2.97 g) was added to admantane-1-carboxylic acid hydrazide (3.88 g) in ethanol (100 ml) and stirred for 30 min. A precipitate formed after about 3 min. The suspension was evaporated to dryness, washed with water and the amidrazone product crystallized from ethanol (4.22 g, 73.2%) m.p 245° (sealed tube). Found: C, 53.98% H, 6.28%; F, 20.0%; N, 14.75%. $C_{13}H_{18}F_3N_3O$ requires: C, 53.97%; H, 6.27%; F, 19.7%; N, 14.53%. The amidrazone (3.0 g)

was heated at reflux with 3M sodium hydroxide solution (40 ml) for 1 hr, cooled, acidified and filtered. The product, 3(5)-(1-Adamantyl)-5(3)-trifluoromethyl-1,2,4-triazole, crystallized from hot benzene, m.p. 277° (2.21 g, 78.5%). Found: C, 57.73%; H, 5.99%; F, 20.9%; N, 15.77%. $C_{13}H_{16}F_3N_3$ requires: C, 57.55%; H, 5.94%; F, 21.0%; N, 15.49%.

In a similar manner, using the appropriate starting materials, the following compounds were prepared.

b. 3(5)-(4-pyridyl)-5(3)-trifluoromethyl-1,2,4-triazole. (m.p. 224° C)

c. 3(5)-phenyl-5(3)-trifluoromethyl-1,2,4triazole. (m.p. 163° C)

d. 3(5)-(4-chlorophenyl)-5(3)-trifluoromethyl-1,2,4-triazole. (m.p 177° C)

e. 3(5)-(3,4-dichlorophenyl)-5(3)-trifluoromethyl-1,2,4-triazole. (m.p. 182° C).

f. 3(5)-(2,3,6-trichlorophenyl)-5(3)-trifluoromethyl-1,2,4-triazole. (m.p. 192° C).

g. 3(5)(4-nitrophenyl)-5(3)-trifluoromethyl-1,2,4-triazole. (m.p. 183° C).

Consistent analyses were obtained for these compounds.

EXAMPLE 21

The new compounds were examined in several biological tests. The acaricidal activity was measured against the larvae of the Australian cattle tick (*Boophilus microplus*). The specificity of interference of the designed compounds with mitochondrial oxidative processes was examined by the differential inhibition of growth of *Saccaromyces cerevisiae* with ethanol or glucose as substrates.

Other biochemical tests carried out with the compounds were the measurement of their effects on the uncoupling of oxidative phosphorylation and the inhibition of energy transfer in the mitochondrial respiration sequences. In the light of a known report on the action of certain acaricides as monoamine oxidase (MAO) inhibitors, the new structures were also examined in this test, and their activity compared to the reported MAO inhibition shown by the potent acaricide N-(2,4-dimethylphenyl)-N'-methyl formamidine (BTS 27271).

METHODS

Acaricide testing

The determinations of mortalities were carried out in packets on 7 - 14 day old larvae of the cattle tick Boophilus microplus using the method described by Stone [1]. Mortalities were counted 24 hours after the application of the compounds. The activities of DDT and BTS 27271 were also determined.

Growth studies

Saccharamyces cerevisiae, strain L410, was grown aerobically at 28° in a salts medium containing 1% Difco yeast extract and 0.5% bacteriological peptone as described by Wallace, P.G. et al.[2] with either ethanol (1% w/v) or glucose (5% w/v) as carbon and energy sources. Cells were innoculated at a concentration of 10 μg of dry weight per ml and grown for 24 hours. Growth was measured as described by Clark-Walker et al.[3], and compared with control incubations.

Oxidative phosphorylation a. Preparation of yeast mitochondria

Yeast mitochondria were prepared as described by Watson, K. et al.[4]. The effects of anti-metabolites on oxidative phosphorylation were determined in a polarograph cell at 30° in the medium described by Haslam, J.M. et al.[5]. Substrates were either succinate (4.0 mM) or ethanol (0.3M). Other additions, where indicated, were Sigma ADP and 2:4-dinitrophenol (DNP).

b. Preparation of rat liver mitochondria

Rat liver mitochondria were prepared by the method described by Hogeboon[6] in a medium containing 0.25M sucrose; 10 mM tris-HCl (pH 7.40); 0.5 mM EDTA and finally suspended in the same medium plus bovine-serum albumin (2 mg/ml). Oxidative phosphorylation was measured polarographically at 30°, as described by Estabrook, R.W. et al.[7]. The incubation medium contained 0.25 M sucrose; 10 mM tris-HCl (pH 7.4); 5 mM $K_2HPO_4$ (pH 7.4); 0.5 mM EDTA and bovine-serum albumin (2 mg/ml). DNP was added and control tests were carried out using n-octyl guanidine [8] and either pyruvate or succinate as substrates.

State 3 and state 4 respiration rates were determined by the method of Chance, B. et al.[9]. Percentage uncoupling in the presence of antimetabolites was calculated from the equation.

100 × Rate in the presence of antimetabolite-State 4 rate /State 3 rate - State 4 rate Percentage inhibition of coupled respiration was calculated from the equation 100 × State 3 rate - State 3 rate plus antimetabolite/- State 3 rate - State 4 rate Relative uncoupling and n-octylguanidine like effects are compared as the concentrations required to give 50% effects ($I_{50}$).

Measurement of monoamine oxidase activities

Purified intact rat liver disrupted were disrupting by treating with triton X-100 (1% w/v) for 20 mins. at 0°-4°. The MAO activity was measured spectrophotometrically at 360 nm as described by Weissbach, H. et al.[10]. The activity of BTS 27271 was determined by this method and the enzyme inhibition for other compounds was expressed relative to its $I_{50}$ value.

REFERENCES

[1] Stone, B.F. (1968). Inheritance of resistance to organophosphorus acaricides in the cattle tick Boophilus microplus. Aust. J. Biol. Sci. 21, 309–319.
[2] Wallace, P.G., Huang, M., and Linnane, A.W. (1968) Influence of medium composition on the cytology of anaerobically grown Saccharomyces cerevisiae. J. Cell Biol. 37, 207–220.
[3] Clark-Walker, G.D., and Linnane, A.W. (1967). The biogenesis of mitochondria in Saccharomyces cerevisiae, J. Cell Biol. 37, 1–14.
[4] Watson, K., Haslam, J.M., and Linnane, A.W. (1970). Biogenesis of mitochondria. The isolation of mitochondrial structures from anaerobically grown Saccharomyces cerevisiae. J. Cell Biol. 46, 88–96.
[5] Haslam, J.M., Proudlock, J.W., and Linnane, A.W. (1971) Biogenesis of mitochondria 20. The effects of altered membrane lipid composition on mitochondrial oxidative phosphyrylation in Saccharomyces cerevisiae. Bioenergetics 2, 351–370.
[6] Hogebocn, G.H. (1955). Fractionation of cell components of animal tissues. Methods of Enzymology (Colowick, S.P. and Kaplan, N.O. editors, Academic Press, New York) 1,16–22.
[7] Estabrook, R. W. (1967). Mitochondrial respiratory control and the polarographic measurement of ADP: 0 ratios. Methods in Enzymology (Colowick, S.P. and Kaplan, N.O., editors, Academic Press, New York) 10, 41–47.
[8] Pressman, B.C. (1963). The effects of guanidine and alkylguanidines on the energy transfer reactions of mitochondria. J. Biol. Chem. 238, 401–409.
[9] Chance, B.T., and Williams, G.R. (1955). Respiratory enzymes in oxidative phosphorylation. J. Biol. Chem. 217, 409–427.
[10] Weissbach, H., Smith, T.E., Dally, J.W., Witkep, B., and Undenfriend, S. (1960). A rapid spectrophotometric assay of monoamine oxidase based on the rate of disappearance of kynuramine. J. Biol. Chem. 235, 1160-1163.

RESULTS

The results of the tests are given in Table I The compounds listed in Table I exhibited various degrees of activity against the larvae of the cattle tick, some with a potency comparable in this test to the activities of several chemical agents previously used for the control of this parasite.

The localization of the biochemical lesion in the mitochondrial oxidative system is shown for a number of the compounds by the higher degree of inhibition of the growth of Saccharomyces cerevisiae using ethanol as a substrate compared to a lesser or no inhibition of the fermentative growth on glucose.

The experiments on compounds of Examples 1, and 3 to 6, (Table I) show an inhibition of State 3 respiration in rat liver mitochondrial preparations with pyruvate as a substrate which was only partially reversed on addition of the uncoupling agent 2:4-dinitrophenol (DNP). However, the inhibition of respiration was fully reversed by DNP with succinate as the substrate. This type of energy transfer inhibition in the mitochondrial oxidation sequence was compared with and found similar to that reported for the action of alkyl guanidines by Pressman [8]. The half-maximal effect of the tertbutyl substituted triazole (Example 5) on State 3 respiration by yeast mitochondira was given by a similar concentration (0.16 mM) to that obtained for the inhibition of the growth of this strain of yeast with ethanol as the substrate (0.10 mM). This indicates that the energy transfer inhibition by a guanidine type of action in the mitochondrial respiratory chain accounts for most of its biochemical activity in the yeast cell.

The triazoles of Examples 20(c), (d) and (e) which have in the heterocyclic nucleus a tautomeric proton linked to nitrogen, show high uncoupling activity in yeast and rat liver mitochondrial preparations.

Additional unexpected activity for compounds of Examples 20(d), 20(e), 12 and 13 was the potent inhibition of rat liver monoamine oxidase which for the triazole of Example 13 was four times that determined for the acaricide BTS 27271 in a similar test.

TABLE I

Acaricidal and biochemical activities of 1,2,4-triazoles

A = Toxicity to Boophilus microplus larvae
B = Inhibition of rat liver monoamine oxidase relative to $I_{50}$ value of BTS 27271 = 100
C = Uncoupling activity of oxidative phosphorylation in rat liver mitochondria
D = Inhibition of the growth of Saccharomyces cerevisiae on two substrates

| Compound of Ex.No. | A $LC_{50}(\%)$ | B Relative inhibition | C $I_{50}$(mM) | D Glucose $I_{50}$(mM) | D Ethanol $I_{50}$(mM) |
|---|---|---|---|---|---|
| 1 | 0.62 | 0 | (Slight uncoupling at 2.0 mM State 3 inhibition) | Slight effect* | 2.5 |
| 3 | 0.60 | 2 | | Slight effect* | 2.5 |
| 4 | 0.52 | 2.5 | | no effect* | slight effect* |
| 5 | 2.16 | 0 | | slight effect* | 1.0 |
| 6 | 0.38 | 5 | | no | slight |
| 7 | 0.61 | 2.5 | — | no effect* | slight effect* |
| 8 | 1.8 | 1 | — | no | no |
| 9 | 1.55 | — | — | — | — |
| 10 | 0.87 | — | — | — | — |
| 11 | 0.50 | 2 | — | no effect* | slight effect* |
| 12 | >1 | 200 | no effect* | no effect* | no effect* |
| 13 | 2.75 | 400 | no effect* | no effect (1.0mM) | no effect (1.0mM) |
| 16 | 0.50 | 0 | no effect* | — | — |
| 20 (c) | 0.60 | 0 | 0.08 | 1.0 | 0.3 |
| 20 (d) | 0.45 | 27 | 0.012 | 0.3 | 0.03 |
| 20 (e) | 0.38 | 42 | 0.0023 | 0.3 | 0.01 |
| BTS 27271 | 0.2;78% | 100 | no effect* | no effect* | no effect* |
| DDT | 0.78 | — | — | — | — |

*tested at 2.0 mM

EXAMPLE 22

Compounds of the invention were tested for their activity against the two-spotted spider mite, *Tetranychus urticae*. In this test, discs of dwarf bean leaf were treated with varying known amounts of the test compound. On each disc, 15 mites were placed and the sample kept under cover. Mortalities were determined after 24 hours and compared with treated controls. The following $LC_{50}$ values were obtained:

TABLE II

| Compound of Examples | $LC_{50}$ Values |
|---|---|
| 7 | 1.4 µg/µl |
| DDT* | >20 µg/µl |

*included for comparision.

The claims defining the invention are as follows:
1. A compound of the group consisting of:
4-phenyl-3-trifluoromethyl-1,2,4-triazole;
4-(4-chlorophenyl)-3-trifluoromethyl-1,2,4-triazole;
4-(2-methylphenyl)-3-trifluoromethyl-1,2,4-triazole;
4-(2-t-butylphenyl)-3-trifluoromethyl-1,2,4-triazole;
4-(2-methoxyphenyl)-3-trifluoromethyl-1,2,4-triazole;
4-(4-ethoxyphenyl)-3-trifluoromethyl-1,2,4-triazole;
4-(4-t-butylphenyl)-3-trifluoromethyl-1,2,4-triazole;
4-(2,4-dimethylphenyl)-3-trifluoromethyl-1,2,4-triazole;
4-(4-chloro-2-methylphenyl)-3-trifluoromethyl-1,2,4-triazole;
3-methyl-4-phenyl-5-trifluoromethyl-1,2,4-triazole;
3,4-bis(4-chlorophenyl)-5-trifluoromethyl-1,2,4-triazole;
1-phenyl-3-trifluoromethyl-1,2,4-triazole;
3-trifluoromethyl-1,2,4-triazole;
3(5)-phenyl-5(3)-trifluoromethyl-1,2,4-triazole;
3(5)-(4-chlorophenyl)-5(3)-trifluoromethyl-1,2,4-triazole; and
3(5)-(3,4-dichlorophenyl)-5(3)-trifluoromethyl-1,2,4-triazole.

2. 1-phenyl-3-trifluoromethyl-1,2,4-triazole.

3. 4-phenyl-3-trifluoromethyl-1,2,4-triazole.

4. A pest control composition comprising an acaricidally effective amount of a triazole compound as defined in claim 1 in admixture with a solid or liquid carrier material.

* * * * *